United States Patent [19]

Higashiguchi et al.

[11] Patent Number: 5,767,974
[45] Date of Patent: Jun. 16, 1998

[54] APPARATUS AND METHOD FOR IDENTIFYING PHOTOMASK PATTERN DEFECTS

[75] Inventors: Hisayoshi Higashiguchi, Itami; Kunihiro Hosono, Tokyo, both of Japan

[73] Assignees: Mitsubishi Denki Kabushiki Kaisha, Tokyo; Ryoden Semiconductor System Engineering Corporation, Hyogo, both of Japan

[21] Appl. No.: 586,152

[22] Filed: Jan. 17, 1996

[30] Foreign Application Priority Data

Feb. 24, 1995 [JP] Japan .................... 7-036912

[51] Int. Cl.$^6$ .................................. G01B 11/00
[52] U.S. Cl. ................................ 356/394
[58] Field of Search ........................ 356/401, 394, 356/390, 389, 391–393, 395–398, 237, 239; 250/559.2, 559.4, 559.41, 559.43, 559.44, 559.45, 559.46

[56] References Cited

U.S. PATENT DOCUMENTS

4,579,455  4/1986  Levy et al. .................... 356/394
5,098,191  3/1992  Noguchi et al. ............... 356/394
5,270,796  12/1993 Tokui et al. ................... 356/394

*Primary Examiner*—K. Hantis
*Attorney, Agent, or Firm*—Leydig, Voit & Mayer, Ltd.

[57] ABSTRACT

An apparatus and method for inspecting photomask pattern defects, discriminating true defects from false ones, efficiently detects only the true defects. The apparatus includes a light source; an irradiation section for transmitting light from the light source to a photomask; a light detecting section for detecting the light passing through transparent parts of the photomask; an image processing section for acquiring image data of the pattern according to signals from the light detecting section; a first condition setting section for setting a coordinate threshold that defines a misregistration defect in the pattern; a second condition setting section for setting an area threshold that defines an area defect of the pattern; a testing section that determines whether the coordinates of a pattern feature and the area of the pattern satisfy the thresholds upon comparison to a second pattern; and an output section for outputting a signal indicating a defect only when at least one of the thresholds is exceeded.

6 Claims, 9 Drawing Sheets

APPARATUS AND METHOD FOR IDENTIFYING PHOTOMASK PATTERN DEFECTS

BACKGROUND OF THE INVENTION

1. Field of the Invention

This invention relates to apparatus and method for inspecting photomask pattern defects and, more particularly, to apparatus and method for inspecting defects in a photomask pattern having a microscopic auxiliary pattern.

2. Description of the Related Art

Figure 1:
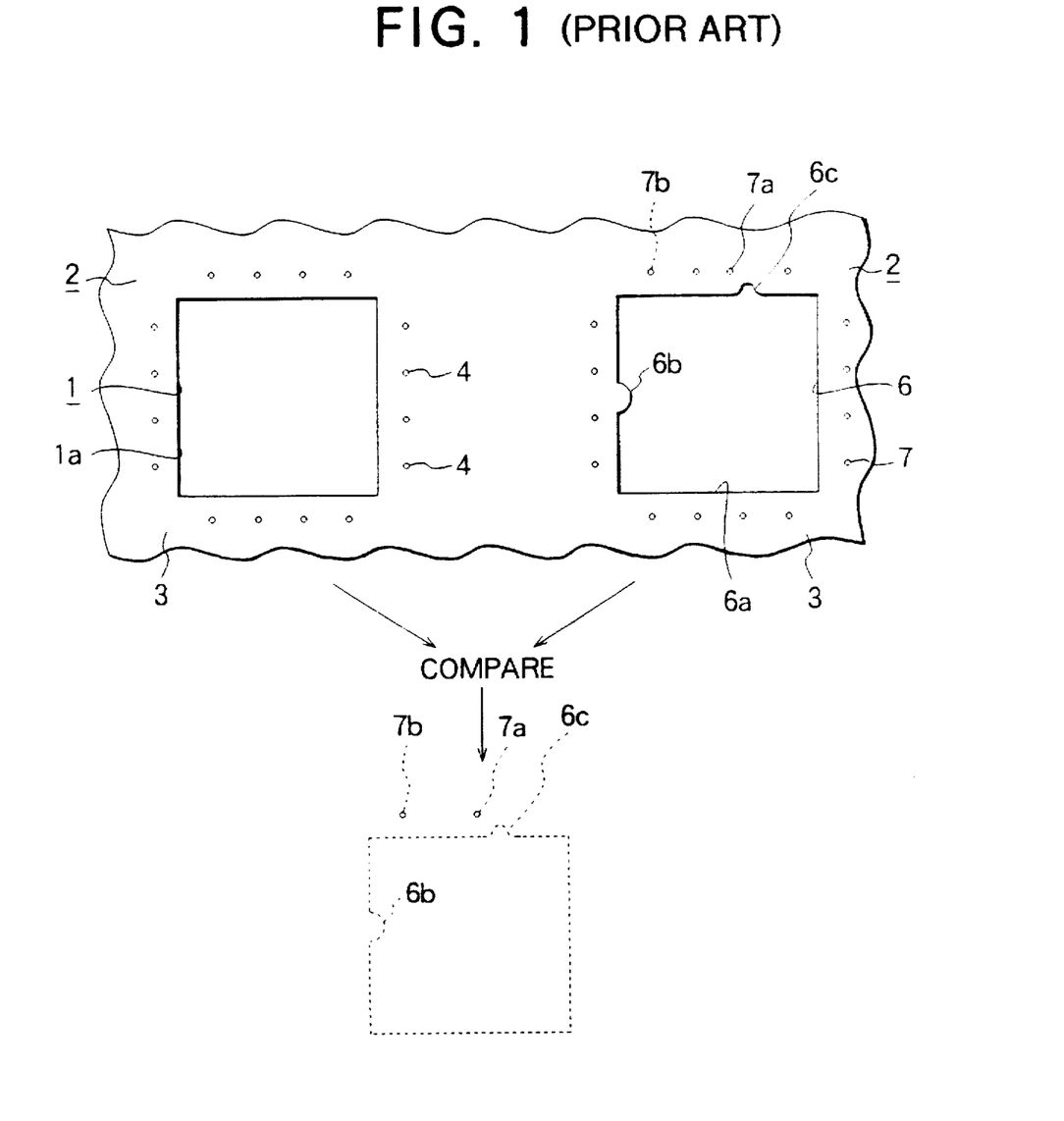
FIG. 1 is a plan view showing an example of a phase shifting mask where a plurality of identical patterns are present.
Figure 2:
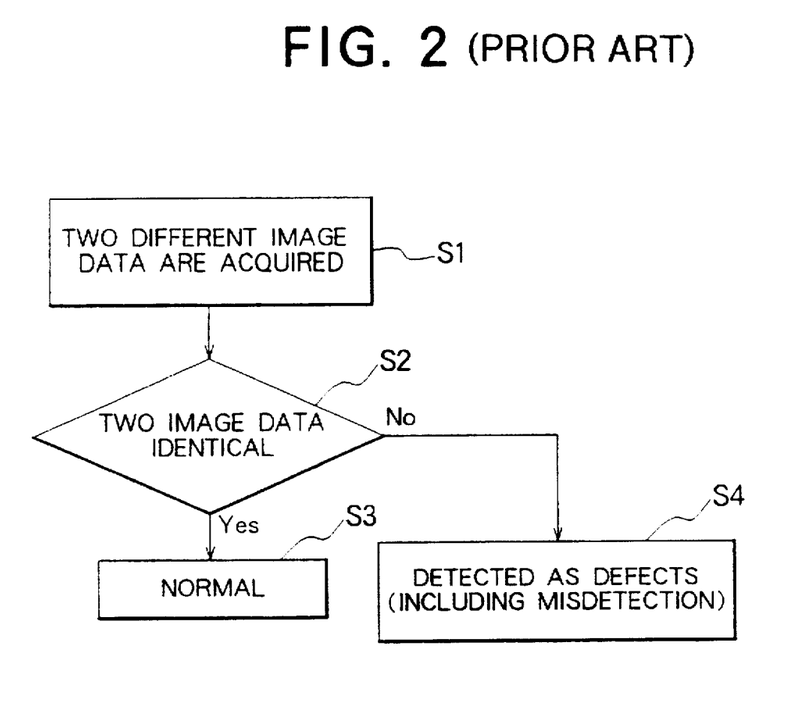
FIG. 2 is a flowchart showing a known method for inspecting photomask pattern defects.
Figure 3:
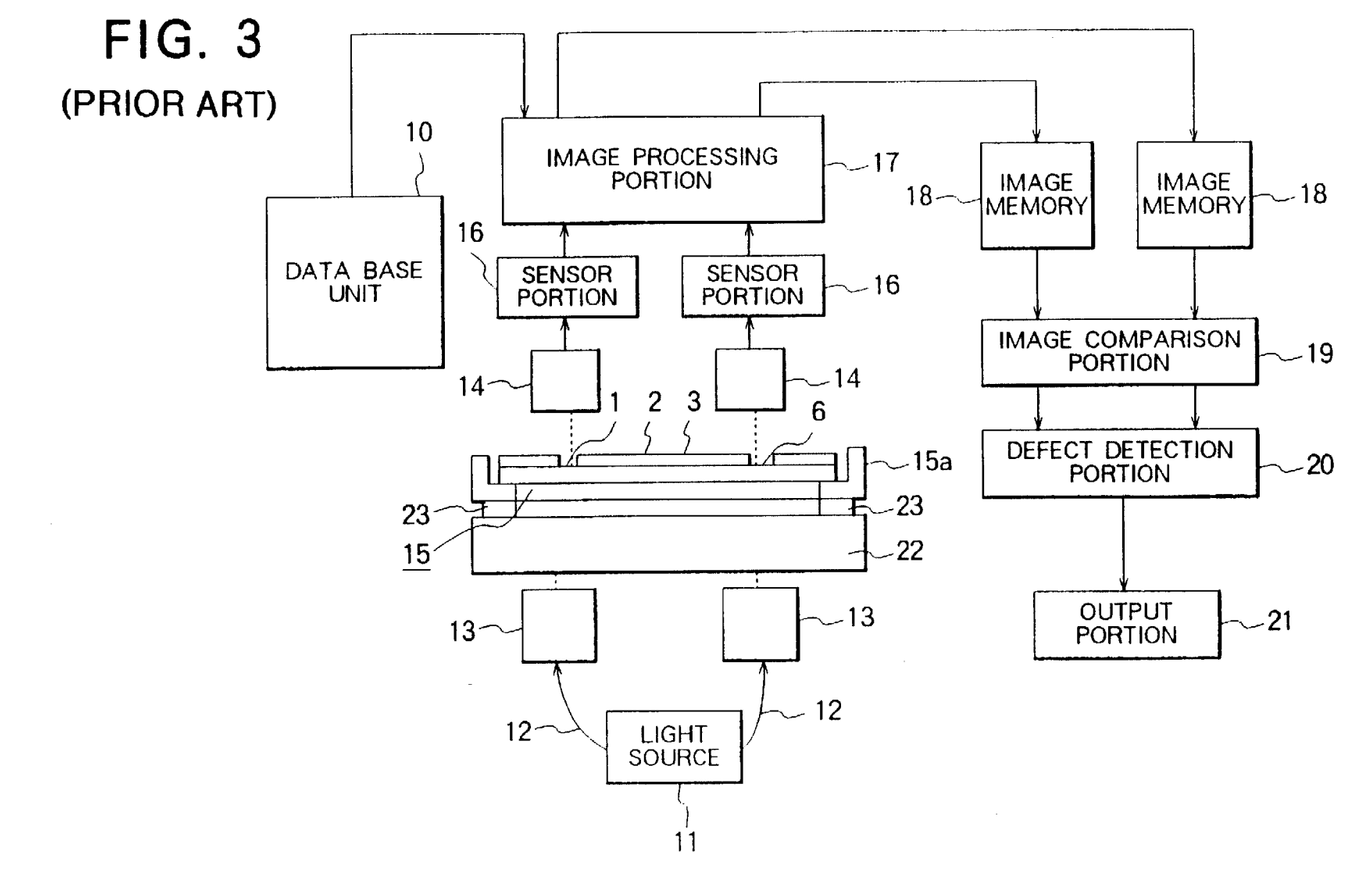
FIG. 3 is a block diagram showing a known apparatus for inspecting photomask pattern defects.
Figure 4:
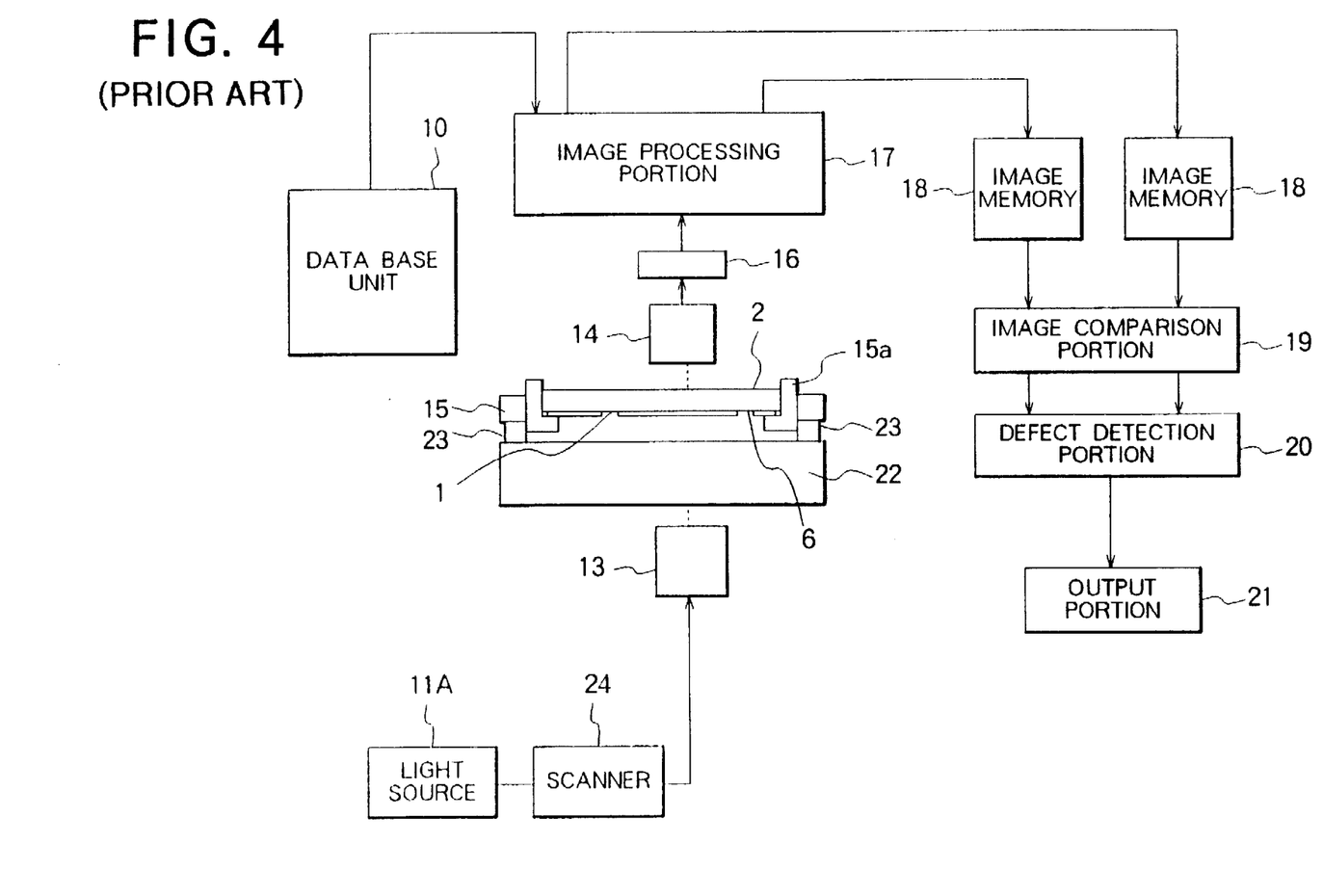
FIG. 4 is a block diagram showing another known apparatus for inspecting a photomask pattern defects.

A photomask is utilized in a semiconductor-device manufacturing process. A pattern on the photomask is transcribed on to a semiconductor wafer so as to be mass-produced. Thus, the photomask itself must be defect-free. Therefore, a defect-detecting or inspection procedure for detecting defects plays an important and necessary role in manufacturing the photomasks. FIG. 1 shows a pattern formed on a photomask, while FIG. 3 and FIG. 4 show a configuration of a known apparatus for inspecting or detecting a photomask pattern defect (hereinafter referred to as an inspection apparatus). In FIG. 1, a phase-shifting mask is shown as an example of a photomask. FIG. 2 is a flowchart showing a known method for inspecting or detecting the photomask pattern defect (hereinafter referred to as an inspection method).

Referring to FIG. 1, reference numerals 1 and 6 indicate cut-out patterns (light passing portions) formed by etching and reference numeral 3 indicates a light shielding portion which blocks the light. In the phase shifting mask 2, when transcribing the pattern on to a semiconductor wafer with a stepper (not shown), the auxiliary patterns 4 and 7 must be provided in parallel along with edges 1a and 6a of patterns 1 and 6 in order to emphasize edges 1a, 6a of transcribed patterns 1, 6. The auxiliary patterns 4 and 7 are formed simultaneously with the patterns 1 and 6 by etching, and are generally microscopically smaller than the patterns 1 and 6. Two cases are generally considered in inspecting the phase shifting mask 2 including these small auxiliary patterns 4 and 7. One method is that inspection is performed by comparing the pattern 1 with the pattern 6 in the case of multi-chip masks etc. where a plurality of the same patterns are formed on the phase shifting mask 2. Another method is that the pattern 1 or pattern 6 on the phase shifting mask 2 is compared to inspection reference data (design data) stored in advance in a data base unit 10 of the inspection apparatus (See FIG. 3). Photo mask defects include: a concavity 6b and a projection 6c in the edge 6a of the pattern 6, a misregistration 7a and omission 7b in the auxiliary pattern 7 shown in FIG. 1, a bridge formation between patterns, and generation of an unwanted light shielding portion (shaded spot) and an unwanted light passing portion (clear spot).

Next, the configuration of the known inspection apparatus is described with reference to FIG. 3. FIG. 3 illustrates the known inspection apparatus for inspecting defects of multi-chip masks in which a plurality of the same patterns are formed on the photomask such as the above-described phase shifting mask 2. The inspection apparatus shown FIG. 3 includes: a pair of irradiation lenses 13 which focus light supplied from a light source 11, which is constituted by a high-pressure mercury lamp etc., via an optical fiber 12 on the photomasks such as a phase shifting mask 2, etc. (hereinafter a phase shifting mask 2 is taken as an example of the photomask); light receiving lenses 14 provided opposite to respective irradiation lenses 13 for receiving separately light which is irradiated from the corresponding irradiation lens 13 and has passed through the phase shifting mask 2; a pair of sensor portions 16 which detect light incident on each light receiving lens 14; an image processing portion 17 which produces image data for the pattern formed on the phase shifting mask 2 according to a detection signal received from each sensor portion 16; a pair of image memories 18 which separately store per pattern the image data produced by the image processing portion 17; an image comparison portion 19 which superimposes and compares the image data stored in the image memory 18; defect detection portion 20 which detects a pattern defect based on a comparison result produced by the image comparison portion 19; and output portion 21 which outputs signals indicating a detected defect to the outside. The inspection apparatus further includes a stage 15 which has a mask holder 15a for holding and supporting the phase shifting mask 2, and a granite base 22 on which the stage 15 is placed so that the stage 15 floats over the base 22 by means of air bearing 23 that is driven by a motor (not shown).

Referring to the inspection apparatus shown in FIG. 3, described below is the inspection method for comparing the same patterns on the phase shifting mask 2 so as to perform inspection. The patterns 1 and 6 are formed on the phase shifting mask 2, as shown in FIG. 1. Light passing through the irradiation lenses 13 is incident respectively on the patterns 1 and 6 on the phase shifting mask 2, and then the light having passed through the phase shifting mask 2 is received by the light receiving lens 14, and is detected by the sensor portion 16. Based on detection signals obtained at the sensor portion 16, image data corresponding to the pattern 1 and pattern 6 formed on the phase shifting mask 2 is produced by the image processing portion 17 (step S1 in FIG. 2). The image data thus produced is separately stored in the image memory 18 per pattern 1 and pattern 6, and is compared at the image comparison portion 19 (step S2). Then, if no difference is found between pattern 1 and pattern 6, it is judged that both patterns have no defect. Then, the inspection result is output as being normal from the output portion 21 (step S3). If there are different points between pattern 1 and pattern 6, such as 6b, 6c, 7a and 7b indicated with broken lines in FIG. 1, those points are recognized as defects and the inspection result is output as being abnormal accordingly (step S4).

Referring still to the inspection apparatus in FIG. 3, described here is another inspection method in which the inspection is carried out in a manner that the pattern 1 on the phase shifting mask 2 is compared to the inspection reference data (design data) stored in advance in the data base unit 10 when, for example, no plural identical patterns are formed on the phase shifting mask 2, etc. Image data on a single pattern is produced utilizing a single irradiation lens 13 and single light receiving lens 14 (step S1). Then, the data image data on pattern 1 is compared to inspection reference data sent from the data base unit 10, and the inspection result is output according to the comparison result (step S3 or step S4).

FIG. 4 illustrates another known inspection apparatus. In this inspection apparatus, there are provided a single irradiation lens 13 and a single light receiving lens 14, and light source 11A is constituted by an argon laser and the like. Image data on the phase shifting mask 2 is acquired by moving the stage 15 and by scanning the laser beam with a scanner 24. The stage 15 is similar to that shown in FIG. 3 except that it is driven by a linear motor. Other construction is identical to that shown in FIG. 3 and a description therefor is omitted here. In the case where there are a plurality of the same patterns on the phase shifting mask 2, image data on a single pattern among a plurality of patterns is acquired and stored in the image memory 18. Next, image data on another pattern is acquired and is stored in another image memory 18. The former image data and the latter image data are compared and inspected. Moreover, if no plural identical patterns are formed on the phase shifting mask 2, the inspection is performed in the same manner as described with reference to FIG. 3 by using the inspection reference data stored in the data base unit 10.

In the known apparatus and method for inspecting the photomask pattern defects by comparing the same patterns on the phase shifting mask, true defects should be detected, such as concavity 6b, projection 6c of the edge 6a, omission 7b and a great degree of misregistration 6c, etc. However, false defects such as a slight difference of light transmission owing to slight difference in size between the auxiliary patterns 4 and almost unrecognizable small misregistration, which should not be detected, are falsely and undesirably recognized as defects, thus causing misdetection to a great degree. Similarly, in known apparatus and methods in which inspection is carried out in a manner that the pattern on the photomask is compared to inspection reference data, a slight difference between the actual pattern and the inspection reference data is detected and is recognized as a false defect. The true wanted defects are buried among these numerous misdetected defects, so that enormous time is wasted on sorting out the false and true defects.

SUMMARY OF THE INVENTION

In view of the foregoing drawbacks, it is therefore an object of the present invention to provide an apparatus and method for inspecting photomask pattern defects which is capable of discriminating true defects from false ones so as to efficiently detect the true defects alone.

According to the present invention, there is provided an apparatus for inspecting photomask pattern defects comprising: a light source; irradiation means for transmitting light supplied from the light source to a photomask; light detecting means for detecting the light emitted by the irradiation means and passing through the photomask; image processing means for acquiring image data of a pattern provided on the photomask according to a signal output from the light detecting means; first condition setting means for setting a first condition which defines whether or not misregistration occurs in the pattern; a second condition setting means for setting a second condition which defines whether or not the size of the pattern is less than a predetermined size; judging means for outputting a judgement signal indicating normality when the coordinate of the pattern satisfies the first condition and the size of the pattern satisfies the second condition in response to the image data acquired by the image processing means; and output means for outputting the judgement signal from the judging means.

The present invention also resides in a method for inspecting photomask pattern defects.

BRIEF DESCRIPTION OF THE DRAWINGS

The present invention will become more readily apparent from the following detailed description of the preferred embodiments of the present invention taken in conjunction with the accompanying drawings, in which.

DESCRIPTION OF THE PREFERRED EMBODIMENT

First Embodiment

Figure 5:
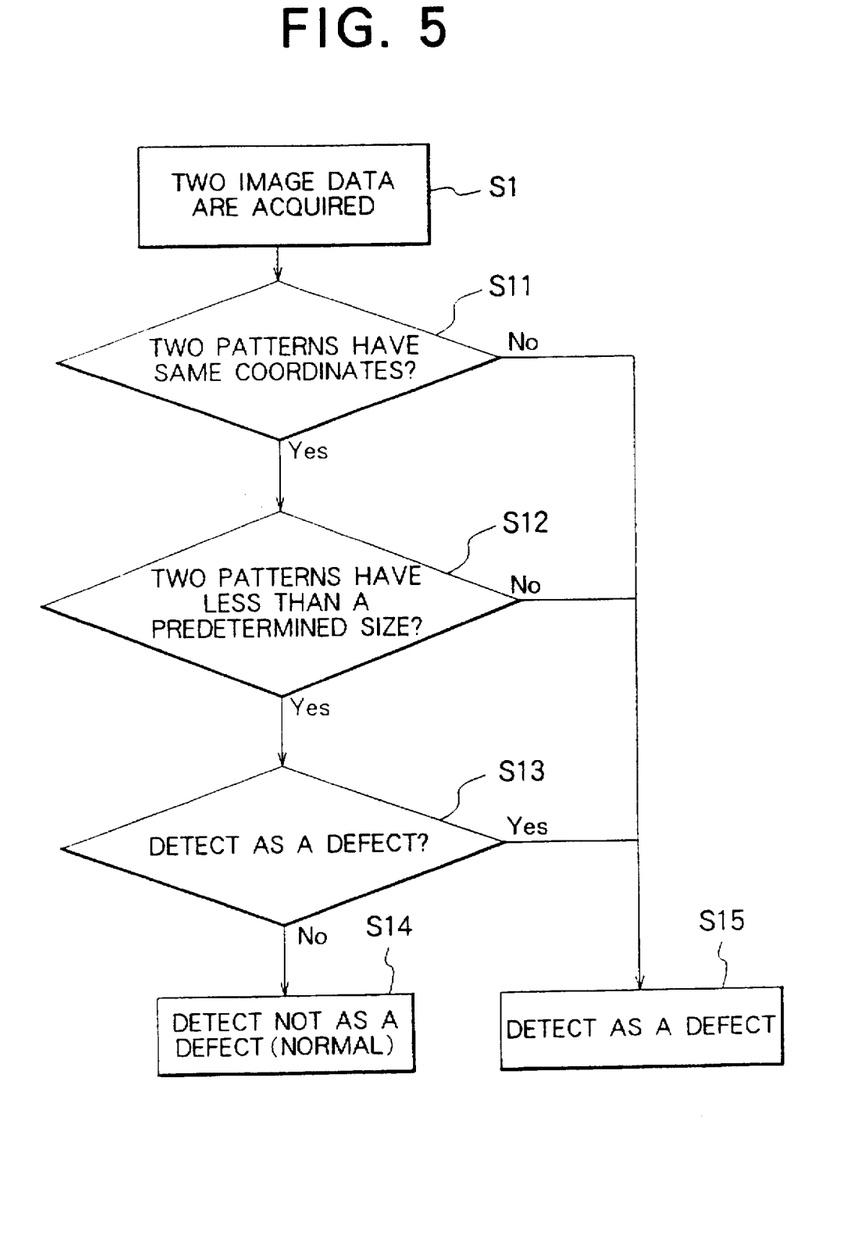
FIG. 5 is a flowchart showing a method for inspecting photomask defects according to the present invention.
Figure 6:
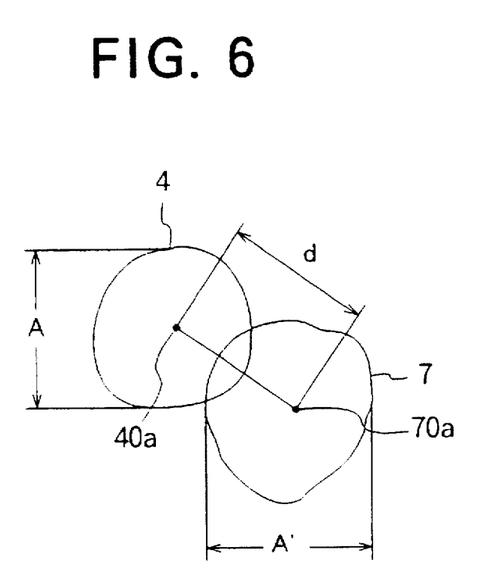
FIG. 6 illustrates auxiliary patterns compared to each other according to the method and apparatus of the First Embodiment.
Figure 7:
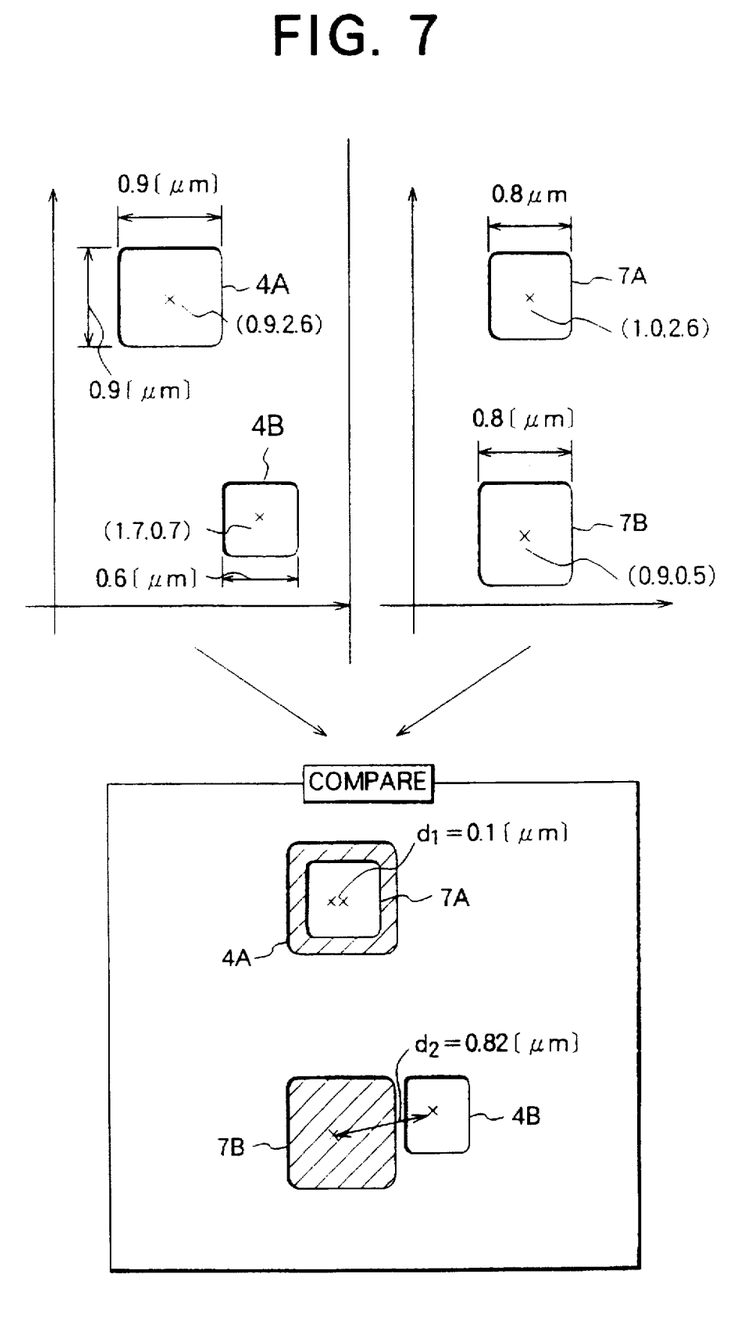
FIG. 7 is a plan view showing specific auxiliary patterns compared to each other according to the method and apparatus of the First Embodiment.

A first embodiment of the present invention will now be described with reference to the drawings. FIG. 5 is a flowchart showing a method for inspecting photomask defects (hereinafter described as an inspection method). Although an apparatus for inspecting photomask defects (hereinafter described as an inspection apparatus) according to the present invention differs from the known inspection apparatus as shown in FIG. 3 and FIG. 4 with respect to functions and operations thereof, a drawing is omitted here since the functions and operations thereof can be described by utilizing FIG. 3 and FIG. 4. First, the inspection method according to the first embodiment will be described. In this first embodiment, a phase shifting mask 2 shown in FIG. 1 is taken as an example of the photomask. In this first embodiment, suppose that there is formed a plurality of the identical patterns (e.g. patterns 1 and 6) on the phase shifting mask 2, and inspection is carried out by comparing these patterns. Notice that auxiliary patterns 4 and 7 in this first embodiment are a plurality of small light passing patterns provided in a row parallel along the edges 1a and 6b of the patterns 1 and 6. The shape of the patterns may be, for example, an approximate circle as shown in FIG. 6 or an approximate rectangle as shown in FIG. 7. As for configuration for the inspection apparatus, FIG. 3 may be referred to and a description therefor is omitted here.

In this first embodiment with reference to FIG. 3, the irradiation lens 13 constitutes irradiation means for transmitting light supplied from the light source 11 to the photomask; the light detecting means includes lens 14 and is for detecting light which is irradiated from irradiation means and has passed through the photomask; the sensor portion 16, image processing portion 17 and image memory 18 constitute image processing means for acquiring image data for the pattern formed on the photomask according to an output signal from the light detecting means; the image comparison portion 19 and defect detection portion 20 constitute a first condition-setting means for setting a first condition which defines whether or not misregistration occurs in the pattern, a second condition-setting means for setting a second condition which defines whether or not the size of the pattern is smaller than a predetermined size, and judging means which determines whether or not the coordinates of the pattern position satisfy the first condition according to the image data acquired by the image processing means, which determines whether or not the size of the pattern satisfies the second condition, and which outputs a judgement signal indicating normality when it is determined that both the first condition and the second condition have been satisfied; and the output portion 21 constitutes output means for externally outputting the judgement signal from the judging means. The data base unit 10 constitutes inspection-reference-data means for storing inspection reference data.

Light passing through the irradiation lens 13 (see FIG. 3) is incident on respectively the patterns 1 and 6 on the phase shifting mask 2, and consequently the light having passed through the phase shifting mask 2 is received by the light receiving lens 14, and detected by the sensor portion 16. Based on detection signals, image data for the patterns 1 and 6 formed on the phase shifting mask 2 is acquired by the image processing portion 17 (step S1 in FIG. 5). The acquired image data is separately stored in the image memory 18 per pattern 1 and pattern 6, and is compared in the image comparison portion 19 by overlapping the acquired images. Operations described up to here are the same as the known practices. However, in this first embodiment according to the present invention, the pattern 1 is compared to the pattern 6 while each auxiliary pattern 4 of the pattern 1 is compared to each auxiliary pattern 7 of the pattern 6 in the defect detection portion 20 as shown in the flowchart shown in FIG. 5 so that whether or not those patterns have the same coordinates is detected (step S11). Then, when the coordinates differ between the patterns 1 and 6 and/or the auxiliary patterns 4 and 7, it is recognized that there is a defect and a result thereof is output accordingly (step S15). Since a slight misregistration of the auxiliary patterns 4 and 7 is a false defect and should not be detected as a defect, a certain constant condition is setup in this first embodiment. Namely, the coordinates are regarded as identical if the following condition is satisfied.

Specifically, when two auxiliary patterns 4 and 7 are compared, for example as shown in FIG. 6, coordinates for respective centers of gravity 40a and 70a are measured and the distance d between the centers of gravity 40a and 70a is calculated. If d is in the range of $$0 \leq d < D \qquad \text{(Equation 1)},$$

it is determined that the two patterns are positioned at the same coordinates. In equation 1, D indicates any positive real number and is set by a user as a parameter of the inspection apparatus. Though the positions for the centers of gravity 40a and 70a are measured in the course of measuring the coordinates in the above example, a measurement method therefor is not limited thereto. It should be appreciated that the coordinates of the edges of the patterns may be measured and other methods will do as long as the coordinates can be properly recognized.

Referring to step S11 shown in the flowchart of FIG. 5, when coordinates are detected as identical utilizing the above method, the sizes of those patterns are measured and it is detected whether or not the detected sizes are less than a predetermined value. Namely, it is detected whether or not those patterns are both auxiliary patterns (step S12) and a defect is determined if either of the pattern sizes is larger than the predetermined value (step S15). If both pattern sizes are less than the predetermined value, it is output as being normal. Moreover, the following method may also be adopted. That is, referring to the flowchart shown in FIG. 5, for example, the transmission factors, etc. of these patterns are detected, if necessary (step S13), and the output portion 21 outputs indicate normality if the compare detected transmission factors are recognized as identical (step S14). The output portion 21 outputs indicate a defect if the detected transmission factors are not recognized as identical (step S15).

The condition for detecting whether or not the pattern sizes are less than the predetermined value in the step S12 may be set as follows. With reference to an example shown in FIG. 6 where the sizes of the auxiliary patterns 4 and 7 are denoted as A and A', respectively, it is determined that both the auxiliary patterns 4 and 7 are smaller than the predetermined size if the following conditions are met, $$a1 < A < a2 \text{ and } a1' < A' < a2' \qquad \text{(Equation 2)},$$

where a1, a2, a1' and a2' indicate any positive real numbers and are set as parameters for the inspection apparatus by the user.

Referring to FIG. 7, further specific conditions are described based on the equations 1 and 2. This time, specific values are substituted in the above equations 1 and 2 so as to define the following equations 3 and 4.

$$0 \leq d \leq A/2 + A'/2 \qquad \text{(Equation 3)},$$

$$0 < A < 1.0 \ (\mu m) \text{ and } 0 < A' < 1.0 \ (\mu m) \qquad \text{(Equation 4)}.$$

In FIG. 7, reference numerals 4A and 4B indicate auxiliary patterns of the pattern 1 (see FIG. 1), while reference numerals 7A and 7B indicate auxiliary patterns of the pattern 6 (see FIG. 1). The auxiliary pattern 4A is such that the size is A=0.9 (μm) and coordinates for the center of gravity are (0.9, 2.6). The auxiliary pattern 4B is such that the size is A=0.6 (μm) and the coordinates for the center of gravity are (1.7, 0.7). The auxiliary pattern 7A is such that the size is A'=0.8 (μm) and the coordinates for the center of gravity are (1.0, 2.6). The auxiliary pattern 7B is such that the size is A=0.8 (μm) and the coordinates for the center of gravity are (0.9, 0.5).

A lower part of FIG. 7 illustrates comparison of the auxiliary pattern 4A to auxiliary pattern 7A while the auxiliary pattern 4B is compared to the auxiliary pattern 7B. Comparing the auxiliary patterns 4A and 7A shows that the sizes of both auxiliary patterns 4A and 7A are less than 1.0 (μm) and the distance d1 between the centers of gravity is d1=0.1 (μm). Applying the condition equation 3 thereto results in 0≤d≤0.85 (μm) and thus d1 satisfies the equation 3. Therefore, these patterns are regarded as identical and will not be detected as including a defect.

Next, comparing the auxiliary patterns 4B and 7B shows that the sizes of both of the auxiliary patterns 4B and 8B are less than 1.0 (μm) and distance d2 between the centers of gravity is d2=0.82 (μm). Similarly, applying the condition equation 3 thereto results in 0≤d≤0.7 (μm) and d2 does not satisfy the equation 3. Therefore, these patterns are not regarded as identical and will be detected as defective even though the sizes of both the auxiliary patterns 4b and 7B are less than 1.0 (μm).

According to the inspection apparatus and inspection method of the present invention, a condition for determining whether or not misregistration occurs in the pattern is set in the first condition-setting means while another condition for determining whether or not the pattern sizes are less than the predetermined value is set in the second condition-setting means, and the result is outputted as normal if those conditions are satisfied. Therefore, as for microscopic patterns such as auxiliary patterns satisfying equation 2, misregistration is determined in a manner that a slight range is permitted as shown in the equation 1. The conditions set forth in the equations 1 and 2 are set by the user by varying the parameters of the inspection apparatus in accordance with usage condition, etc. Thus, in the phase shifting mask 2 including the small auxiliary patterns, the user can easily discriminate true defects from false ones so as to detect the true defects alone. Therefore, misdetection in which false defects are detected is minimized, and working efficiency is greatly improved.

Moreover, since there are provided at least two irradiation means and light defective means, respectively, the patterns are compared if there are a plurality of identical patterns on the photomask. A condition for determining whether or not those coordinates are identical is set in the first condition-setting means. The result will not be output as a defect if those coordinates are same and the pattern sizes are less than the predetermined value, so that at least two patterns can be inspected simultaneously.

Though in the first embodiment the inspection apparatus having the configuration shown in FIG. 3 is introduced as an example, the inspection apparatus shown in FIG. 4 can also be utilized. Moreover, as for the inspection method, the first embodiment can be adapted and incorporated to any known method.

Moreover, in the case where the inspection is performed by comparing the pattern on the photomask to the inspection reference data stored in the inspection-reference-data storage means, a condition for determining whether or not those coordinates are the same is set in the first condition-setting means. If those coordinates are the same and the patterns are less than the predetermined size, the result will not be output as a defect. Therefore, the same advantageous effects as described above can be obtained and the true defects can be further accurately detected since the pattern is compared to the inspection reference data.

Second Embodiment

In the first embodiment, the phase shifting mask is depicted as an example of a photomask, and patterns having the auxiliary patterns of the shape shown in FIG. 1 are specifically described as the pattern and auxiliary pattern formed on the photomask. The pattern shape is not limited thereto. The inspection apparatus and inspection method according to the present invention can be applied to other photomasks and other patterns of various shapes and auxiliary patterns. Some of those examples will be described below.

Figure 8:
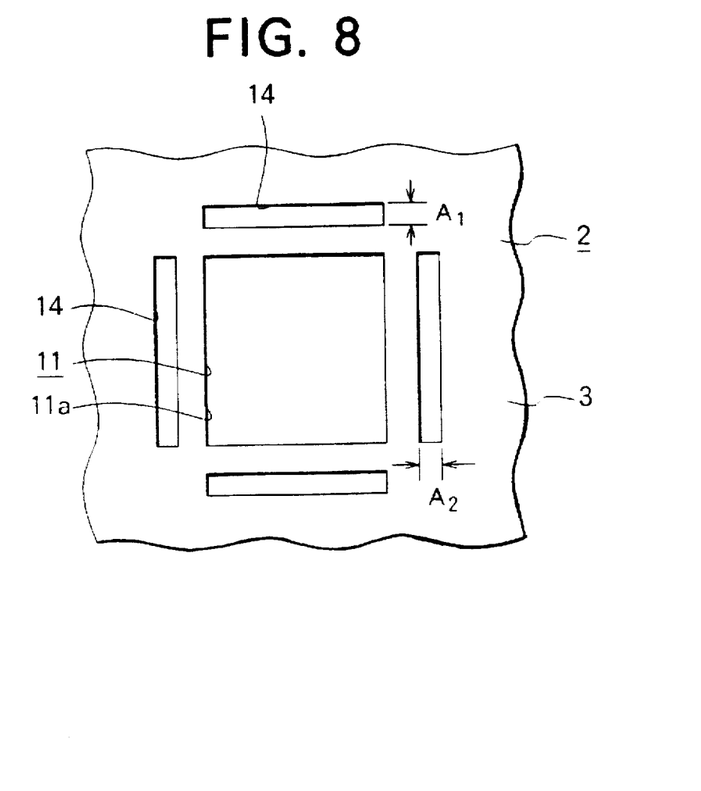
FIG. 8 is a plan view showing another example of as phase shifting mask.

In the phase shifting mask, besides the example shown in FIG. 1 there may be used an auxiliary pattern 14 comprising narrow rectangular cut-out patterns parallel to each edge 11a of pattern 11 shown in FIG. 8. In this case, the inspection is similar to the first embodiment according to the flow shown in FIG. 5. The steps S11 and S12 will be described here, and the description for other steps similar to the first embodiment will be omitted. In this second embodiment, when there are a plurality of the same patterns on the phase shifting mask 2, these patterns may be compared to perform the inspection. Moreover, the inspection may be performed in a manner that the patterns on the phase shifting mask are compared to the inspection reference data (design data) stored in advance in the data base unit 10 of the inspection apparatus.

In employing any of the above methods where the inspection is performed by comparing the auxiliary patterns 14, referring to the step S1 shown in FIG. 5, the image data for the patterns 11 and auxiliary pattern 14 are first stored in the image memory 18 (see FIG. 3 and FIG. 4). Next, in the step S11, the coordinates of the auxiliary pattern 14 are measured according to the image data so that whether they are identical is determined. In the case where two auxiliary patterns 14 are compared, if the distance d between coordinates corresponding thereto satisfies the following equation 5, they are regarded as having similar coordinates $$0 \leq d < D \qquad \text{(Equation 5)},$$

where D is any positive real number which is set as a parameter for the inspection apparatus. Moreover, in the case where the auxiliary pattern 14 is compared to the inspection reference data, if the distance d between coordinates satisfies also the equation 5, they are regarded as having the same coordinates. The centers of gravity can be used as the coordinates as in the first embodiment, and the coordinates of either end of the auxiliary patterns 14 may be used.

When the coordinates are determined as identical, the next step S12 is to determine whether or not the sizes A1 and A2 of thus compared auxiliary patterns 14 are both less than the predetermined value. Namely, it is determined whether or not the following equation 6 is satisfied;

$$a1 < A1 < a2 \text{ and } a1' < A2 < a2' \qquad \text{(Equation 6)}.$$

If the equation 6 is satisfied, it is determined that the auxiliary patterns 14 thus compared are both smaller than the predetermined size. In the equation 6, a1, a2, a1' and a2' indicate any positive real numbers and are set as parameters for the inspection apparatus.

Similar to the first embodiment, true defects are discriminated from false defects in the phase shifting mask 2 including the microscopic auxiliary patterns in the second embodiment. Therefore, only the true defects can be detected, so that misdetection in which false defects are also detected is minimized and the working efficiency is greatly improved.

Third Embodiment

The third embodiment will be described with reference to FIG. 9, taking example of optical proximity correction (OPC) mask as a photomask. In the OPC mask, corners are generally likely to be transcribed into a round shape when a rectangular pattern is transcribed. In order to correct it, as an example for the OPC mask there may be provided an auxiliary pattern 24, including rectangular cut-out patterns, having corners provided on extensions of the diagonal lines of the principal pattern. Thereby, when the pattern 21 is transcribed onto the wafer by the stepper (not shown), the four corners of the pattern 21 transcribed are emphasized by the auxiliary patterns 24, so that the transcribed patterns 21 will approach a rectangular shape.

In this case too, the inspection is performed similarly to the first and second embodiments according to the flow shown in FIG. 5 and it is determined whether or not the coordinates of the auxiliary patterns 24 thus compared are identical in the step 11 by utilizing the image data acquired in step 1. Specifically, for example, as shown in the first and second embodiments, the coordinates for the centers of gravity or the ends thereof are obtained. Then, those patterns are regarded as identical if the distance therebetween satisfies the equation 1.

Next, in the step S12, it is determined whether or not the sizes of the auxiliary patterns 24 thus compared are less than the predetermined size. Specifically, for example, it may be regarded that there is no defect if equation 7 below is satisfied.

$a1 < A3 < a2$ (Equation 7), where a1 and a2 are any positive real numbers and are set as parameters for the inspection apparatus.

Similar to the first and second embodiments, by employing the third embodiment, the true defects are discriminated from the false ones in the phase shifting mask 2 including the microscopic auxiliary patterns. Thus, the true defects can be detected, so that misdetection in which false defects are detected is minimized and the working efficiency is greatly improved.

Figure 9:
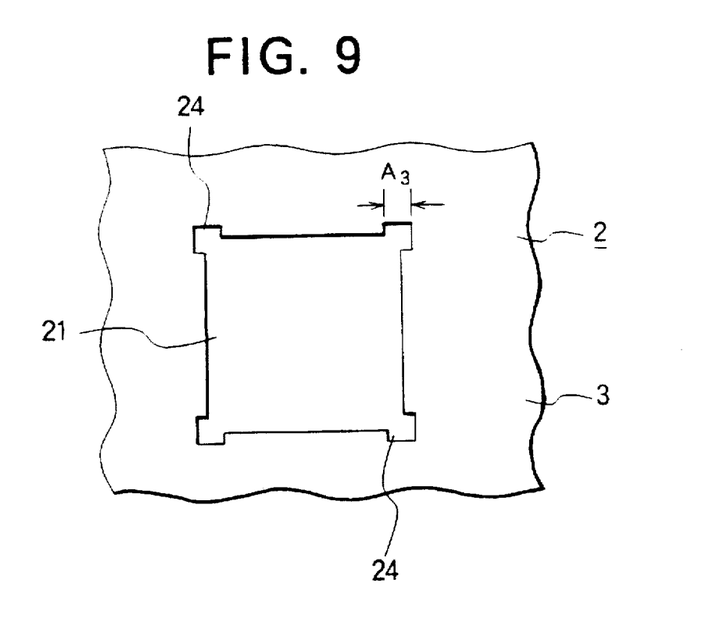
FIG. 9 is a plan view showing an example of an OPC mask.
Figure 10:
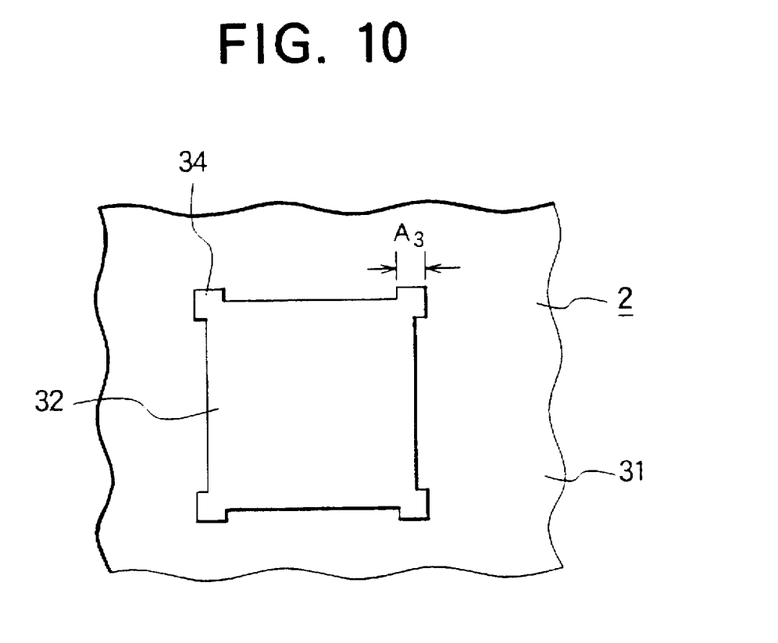
FIG. 10 is a plan view showing another example of an OPC mask.

As another example for the OPC mask pattern, there is a pattern shown in FIG. 10 where a light shielding portion 3 and a light passing portion 21 and 24 comprised of pattern 21 and auxiliary pattern 24 shown in FIG. 9 are reversed. Namely, in this pattern shown in FIG. 10, patterns 32 and 34 are the light shielding portion and a region marked with reference numeral 31 is a light passing portion. Therefore, in this example, the auxiliary pattern 34 comprised of a small and approximately rectangular or square pattern is provided at four corners of the pattern 32 comprised of a left-out pattern. As a result, angular portions of the transcribing pattern of the patterns 32 are emphasized, so that they will not be round-shaped and will approach a rectangular shape. Namely, similar to the example shown in FIG. 9, the light shielding portion and light passing portion of the pattern are simply reversed. Therefore, performing the inspection by utilizing the same inspection apparatus and method depicted in FIG. 9 gives rise to similar advantageous effects in this example. Moreover, the inspection apparatus and method according to the present invention can be adapted to a pattern whose shape is other than the OPC mask described in the above example.

What is claimed is:

1. An apparatus for identifying photomask pattern defects comprising:

a light source;

irradiation means for transmitting light supplied from said light source to a photomask;

light detecting means for detecting light transmitted by said irradiation means and passing through the photomask;

image processing means for acquiring image data for a pattern provided on the photomask according to a signal output from said light detecting means;

first condition setting means for setting a first condition that defines whether a misregistration relative to a test registration is present in the pattern;

second condition setting means for setting a second condition that defines whether the pattern has a size less than a test size;

testing means for outputting a determination signal indicating normality when a coordinate of the pattern satisfies the first condition and the size of the pattern satisfies the second condition according to the image data; and output means for outputting the determination signal.

2. The apparatus as claimed in claim 1, comprising at least two of said irradiation means and at least two of said light detecting means, wherein at least two possibly identical patterns are provided on the photomask, and, said testing means comprises:

an image comparison portion for comparing the image data for the two possibly identical patterns acquired by said image processing means from said light detecting means;

a position testing portion for determining whether coordinates of the patterns satisfy the first condition according to a comparison result from said image comparison portion;

a size testing portion for determining whether sizes of the patterns satisfy said second condition according to the comparison result of said image comparison portion; and an outputting portion for outputting a signal indicating normality when the first and second conditions are met based on signals from said position testing portion and said size testing portion.

3. The apparatus as claimed in claim 1, further comprising inspection-reference-data storage means for storing inspection reference data, wherein said testing means comprises:

a image comparison portion for comparing image data acquired by said image processing means with the inspection reference data;

a position testing portion for determining whether a coordinate of the pattern satisfies the first condition according to a comparison result of said image comparison portion;

a size testing portion for determining whether the size of the pattern satisfies the second condition according to the comparison result of said image comparison portion; and an outputting portion for outputting a signal indicating normality when the first and second conditions are met based on signals from said position testing portion and said size testing portion.

4. The apparatus as claimed in claim 2 wherein the first condition requires that a distance d between corresponding points, in the image data, of at least two possibly identical patterns acquired by said image processing means satisfy $$0 \leq d < D,$$

where D is any positive real number.

5. The apparatus as claimed in claim 3 wherein the first condition requires that a distance d between corresponding points, in the image data, acquired by said image processing means and the inspection reference data, respectively, satisfy $$0 \leq d < D,$$

where D is any positive real number.

6. A method for identifying photomask pattern defects, comprising:

irradiating a photomask with a light;

detecting the light passing through the photomask;

acquiring image data of a pattern on the photomask based on detecting the light;

determining whether a first condition defining a misregistration relative to a test registration is present in the pattern from the image data acquired;

determining whether a second condition defining whether the size of the pattern is less than a test size is met from the image data acquired; and outputting a signal indicating normality when both of the first and second conditions are met.

\* \* \* \* \*